US008630424B2

(12) United States Patent
Slapak et al.

(10) Patent No.: US 8,630,424 B2
(45) **Date of Patent: *Jan. 14, 2014**

(54) ACTIVE NOISE CONTROL SYSTEM AND METHOD

(75) Inventors: Alon Slapak, Mazor (IL); Yehuda Meiman, Rishon Letzion (IL); Gedalin Konstantin, Ashdod (IL)

(73) Assignee: Silentium Ltd., Rehovot (IL)

( * ) Notice: Subject to any disclaimer, the term of this patent is extended or adjusted under 35 U.S.C. 154(b) by 377 days.

This patent is subject to a terminal disclaimer.

(21) Appl. No.: 12/941,145

(22) Filed: Nov. 8, 2010

(65) Prior Publication Data

US 2011/0116645 A1 May 19, 2011

Related U.S. Application Data

(63) Continuation of application No. 10/573,060, filed as application No. PCT/IL2004/000863 on Sep. 19, 2004, now Pat. No. 7,853,024, which is a continuation-in-part of application No. 09/120,973, filed on Jul. 22, 1998, now Pat. No. 7,317,801.

(60) Provisional application No. 60/503,471, filed on Sep. 17, 2003.

(30) Foreign Application Priority Data

Aug. 14, 1997 (IL) ........................................ 121555

(51) Int. Cl.
*A61F 11/06* (2006.01)

(52) U.S. Cl.
USPC ... 381/71.12; 381/71.1; 381/71.7; 381/71.11; 381/71.8; 381/71.2

(58) Field of Classification Search
USPC .......................... 381/71.1–71.9, 71.11–71.14
See application file for complete search history.

(56) References Cited

U.S. PATENT DOCUMENTS

| | | | |
|---|---|---|---|
| 4,025,724 | A | 5/1977 | Davidson, Jr. et al. |
| 4,965,832 | A | 10/1990 | Edwards et al. |
| 5,117,401 | A | 5/1992 | Feintuch |
| 5,182,774 | A | 1/1993 | Bourk |
| 5,271,062 | A | 12/1993 | Sugita et al. |

(Continued)

FOREIGN PATENT DOCUMENTS

| | | | |
|---|---|---|---|
| EP | 0 759 606 | A2 | 2/1997 |
| EP | 0 818 771 | A2 | 1/1998 |

(Continued)

OTHER PUBLICATIONS

Office Action for U.S. Appl. No. 10/573,060 mailed on Oct. 2, 2008; 16 pages.

(Continued)

*Primary Examiner* — Disler Paul
(74) *Attorney, Agent, or Firm* — Shichrur & Co.

(57) ABSTRACT

An Active Noise Control (ANC) for controlling a noise produced by a noise source may include an acoustic sensor (212) to sense a noise pattern and to produce a noise signal corresponding to the sensed noise pattern, an estimator (202) to produce a predicted noise signal by applying an estimation function to the noise signal, and an acoustic transducer (216) to produce a noise destructive pattern based on the predicted noise signal.

20 Claims, 4 Drawing Sheets

(56) References Cited

U.S. PATENT DOCUMENTS

| | | | | |
|---|---|---|---|---|
| 5,343,713 | A | 9/1994 | Okabe et al. | |
| 5,347,586 | A | 9/1994 | Hill et al. | |
| 5,365,594 | A | 11/1994 | Ross et al. | |
| 5,410,607 | A | 4/1995 | Mason et al. | |
| 5,471,537 | A | 11/1995 | Castwall | |
| 5,475,731 | A | 12/1995 | Rasmusson | |
| 5,519,637 | A | 5/1996 | Mathur | |
| 5,553,154 | A | 9/1996 | Tamamura et al. | |
| 5,602,927 | A | 2/1997 | Tamamura et al. | |
| 5,613,009 | A | 3/1997 | Miyazaki et al. | |
| 5,618,010 | A | 4/1997 | Pla et al. | |
| 5,627,896 | A | 5/1997 | Southward et al. | |
| 5,680,393 | A | 10/1997 | Bourmeyster et al. | |
| 5,680,450 | A | 10/1997 | Dent et al. | |
| 5,694,476 | A | 12/1997 | Klippel | |
| 5,745,731 | A | 4/1998 | Kim et al. | |
| 5,748,749 | A | 5/1998 | Miller et al. | |
| 5,768,398 | A | 6/1998 | Janse et al. | |
| 5,812,973 | A | 9/1998 | Wang | |
| 5,978,489 | A * | 11/1999 | Wan | 381/71.11 |
| 6,005,952 | A | 12/1999 | Klippel | |
| 6,084,971 | A | 7/2000 | McLean | |
| 6,160,392 | A | 12/2000 | Shin | |
| 6,160,892 | A | 12/2000 | Ver | |
| 6,181,753 | B1 | 1/2001 | Takada et al. | |
| 6,351,532 | B1 | 2/2002 | Takada et al. | |
| 6,535,609 | B1 | 3/2003 | Finn et al. | |
| 6,895,094 | B1 * | 5/2005 | Scalart et al. | 381/66 |
| 6,944,304 | B1 | 9/2005 | Dance et al. | |
| 7,317,801 | B1 | 1/2008 | Amir | |
| 2002/0080978 | A1 | 6/2002 | Kakuhari et al. | |
| 2003/0103635 | A1 * | 6/2003 | Wright et al. | 381/93 |
| 2003/0112980 | A1 | 6/2003 | Vaishya | |

FOREIGN PATENT DOCUMENTS

| | | |
|---|---|---|
| EP | 0 903 726 A2 | 3/1999 |
| EP | 0 973 151 A2 | 1/2000 |
| EP | 1414021 | 4/2004 |
| WO | 02/32356 A1 | 4/2002 |

OTHER PUBLICATIONS

Final Office Action for U.S. Appl. No. 10/573,060 mailed on Apr. 30, 2009; 17 pages.

Office Action for U.S. Appl. No. 10/573,060 mailed on Sep. 4, 2009; 19 pages.

Final Office Action for U.S. Appl. No. 10/573,060 mailed on Feb. 4, 2010; 22 pages.

Search Report for European patent application 02 02 3483 mailed on Apr. 16, 2003; 3 pages.

Office Action for European patent application 02 02 3483 mailed on Jan. 31, 2005; 4 pages.

Office Action for European patent application 02 02 3483 mailed on Jul. 27, 2006; 3 pages.

Written Opinion and Search Report for PCT/IL04/00863 mailed on Feb. 25, 2005; 4 pages.

Office Action for European patent application 02 02 3483 mailed on Apr. 11, 2005; 4 pages.

Office Action for Korean patent application 10-2006-7007389 mailed on Feb. 24, 2011; 10 pages.

Office Action for U.S. Appl. No. 09/120,973 mailed on Jul. 17, 2003; 10 pages.

Office Action for U.S. Appl. No. 09/120,973 mailed on Sep. 12, 2003; 8 pages.

Office Action for U.S. Appl. No. 09/120,973 mailed on Mar. 24, 2004; 7 pages.

Office Action for U.S. Appl. No. 09/120,973 mailed on Jul. 12, 2004; 8 pages.

Office Action for U.S. Appl. No. 09/120,973 mailed on Dec. 16, 2004; 9 pages.

Office Action for U.S. Appl. No. 09/120,973 mailed on Dec. 15, 2005; 7 pages.

* cited by examiner

ACTIVE NOISE CONTROL SYSTEM AND METHOD

CROSS-REFERENCE TO RELATED APPLICATIONS

This application is a continuation application of U.S. patent application Ser. No. 10/573,060, filed Mar. 20, 2006 which is a National Phase filing of PCT/IL2004/000863, filed on Sep. 19, 2004, which in turn claims priority from U.S. Provisional Application No. 60/503,471, filed Sep. 17, 2003 and is a Continuation in Part of U.S. application Ser. No. 09/120,973, filed Jul. 22, 1998, which claims the benefit of Israel Patent Application No. 121555, filed Aug. 14, 1997. The entire disclosures of the above-referenced these three applications is are incorporated herein by reference.

FIELD OF THE INVENTION

The invention relates to the field of active noise control.

BACKGROUND

Conventional passive noise control systems may include "insulation" elements, silencers, vibration mounts, damping treatments, absorptive treatments, e.g., ceiling tiles, and/or conventional mufflers, e.g., mufflers as may be used in the automobile industry. The dimensions and/or mass of such passive noise control systems may usually depend on the acoustic pattern length of the noise intended to be reduced. Generally, passive noise control systems implemented to reduce noises of relatively low frequencies are bulky, large, heavy and/or expensive.

SUMMARY

According to embodiments of the invention, Active Noise Control (ANC) may be used to reduce noise energy and wave amplitude of a source noise pattern via an ANC sound system, which produces a noise-destructive pattern related to the source noise pattern such that a reduced noise zone may be created.

According to an exemplary embodiment of the invention, the ANC system may include an acoustic sensor, e.g., a microphone, to sense a noise pattern and to produce a noise signal corresponding to the sensed noise pattern; an estimator to produce a predicted noise signal by applying an estimation function to the noise signal; and an acoustic transducer, e.g., a speaker, to produce a noise destructive pattern based on the predicted noise signal.

According to some exemplary embodiments of the invention, the estimation function may include a non-linear estimation function, e.g., a radial basis function.

The estimator may be able to adapt one or more parameters of the estimation function based on a noise error at a predetermined location. For example, the ANC system may include an error evaluator to evaluate the noise error based on the noise signal and the predicted noise signal. Additionally or alternatively, the system may include an error sensing acoustic sensor to sense the noise error at the predetermined location.

The error evaluator may include a speaker transfer function module to produce an estimation of the noise destructive pattern, e.g., by applying a speaker transfer function to the predicted noise signal; a modulation transfer function module to produce an estimation of the noise pattern at the predetermined location, e.g., by applying a modulation transfer function to the noise signal; and a subtractor to subtract the estimation of the noise destructive pattern from the estimation of the noise pattern.

According to some exemplary embodiments, the estimator may be able to adapt the one or more parameters based on a predetermined criterion. For example, the estimator may be able to reduce, e.g., minimize, the error value by adapting the one or more parameters.

According to another exemplary embodiment of the invention, the ANC system may include a primary acoustic sensor, e.g., a microphone, to sense a noise pattern and to produce a corresponding primary noise signal; at least one secondary acoustic sensor, e.g., microphone, to sense a residual noise pattern and to produce at least one secondary noise signal corresponding to the residual noise pattern sensed by the at least one secondary microphone, respectively, wherein the at least one secondary acoustic sensor is separated from the noise source by a distance larger than a distance between the primary acoustic sensor and the noise source; and a controller to control an acoustic transducer to produce a noise destructive pattern based on the primary noise signal and the at least one secondary noise signal.

The controller may include, for example, a primary estimator to produce a predicted primary signal, e.g., by applying a primary estimation function to the primary noise signal; and at least one secondary estimator to produce at least one predicted secondary signal by applying at least one secondary estimation function to the at least one secondary noise signal, respectively.

The primary estimator may be able, for example, to iteratively adapt one or more parameters of the primary estimation function based on a noise error. The at least one secondary estimator may be able, for example, to iteratively adapt one or more parameters of the at least one secondary estimation function, respectively, based on the noise error.

The controller may control the acoustic transducer based on a combination of the predicted primary signal and the at least one predicted secondary signal.

BRIEF DESCRIPTION OF THE DRAWINGS

The subject matter regarded as the invention is particularly pointed out and distinctly claimed in the concluding portion of the specification. The invention, however, both as to organization and method of operation, together with objects, features and advantages thereof, may best be understood by reference to the following detailed description when read with the accompanied drawings in which:

Figure 1:
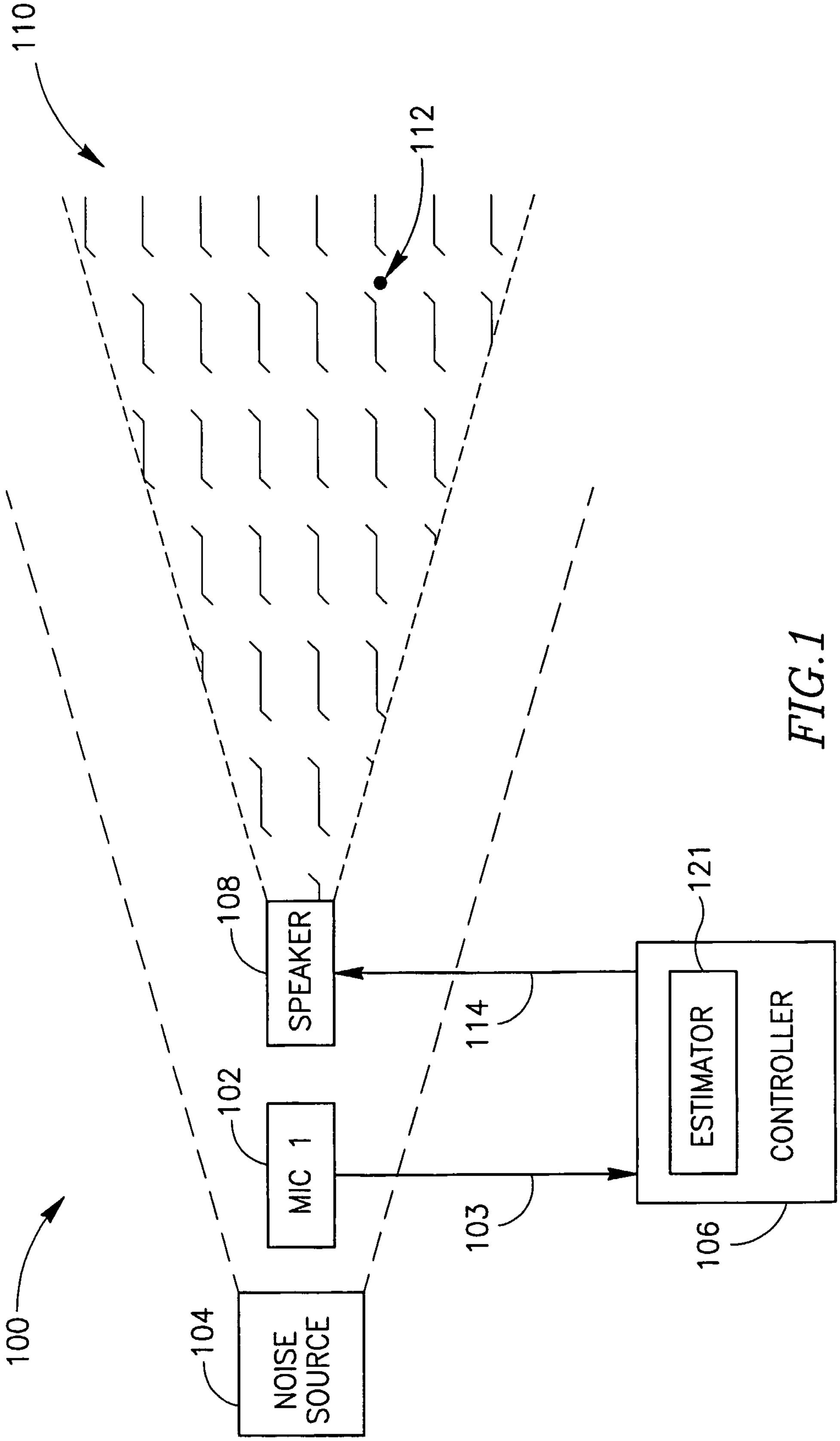
FIG. 1 is a schematic illustration of an active noise control system according to an exemplary embodiment of the invention.

It will be appreciated that for simplicity and clarity of illustration, elements shown in the drawings have not necessarily been drawn accurately or to scale. For example, the dimensions of some of the elements may be exaggerated relative to other elements for clarity or several physical components included in one functional block or element. Further, where considered appropriate, reference numerals may be repeated among the drawings to indicate corresponding or analogous elements. Moreover, some of the blocks depicted in the drawings may be combined into a single function.

DETAILED DESCRIPTION

In the following detailed description, numerous specific details are set forth in order to provide a thorough understanding of the invention. However, it will be understood by those of ordinary skill in the art that the present invention may be practiced without these specific details. In other instances, well-known methods, procedures, components and circuits may not have been described in detail so as not to obscure the present invention.

According to embodiments of the invention, Active Noise Control (ANC) may be used to reduce noise energy and wave amplitude of a source noise pattern, e.g., including one or more acoustic waves, via an ANC sound system, which produces a noise-destructive pattern, e.g., including one or more acoustic waves, related to the source noise pattern such that a reduced noise zone may be created.

Embodiments of the invention include ANC systems and methods, which may be efficiently implemented for reducing undesirable noises, e.g., at least noises of generally low frequencies, as described below.

Certain aspects of ANC methods and systems, in accordance with some exemplary embodiments of the invention, are described in U.S. patent application Ser. No. 09/120,973, filed Jul. 22, 1998, entitled “ACTIVE ACOUSTIC NOISE REDUCTION SYSTEM”; and in European Patent Application 02023483.7, filed Oct. 21, 2002, entitled “ACTIVE ACOUSTIC NOISE REDUCTION SYSTEM”, and published Apr. 28, 2004 as publication number 1414021. The entire disclosure of both of these applications is incorporated herein by reference.

Reference is made to FIG. 1, which schematically illustrates an ANC system 100 according to an exemplary embodiment of the invention.

ANC system 100 may include, for example, a acoustic sensor, e.g., a microphone 102, denoted MIC1, to sense the noise energy and/or wave amplitude of a noise pattern produced by a noise source 104. Microphone 102 may include any suitable microphone able to generate an output noise signal 103, corresponding to the noise pattern sensed by microphone 112. For example, microphone 102 may include microphone Part No. ECM6AP, available from ARIO Electronics Co. Ltd., Taoyuan, Taiwan. Noise signal 103 may include, for example, a sequence of N samples per second. For example, N may be 1000 samples per second, e.g., if microphone 103 operates at a sampling rate of about 10 KHz.

ANC system 100 may also include an acoustic transducer, e.g., a speaker 108, and a controller 106 to control speaker 108 to produce a noise destructive pattern to reduce or cancel the noise energy and/or wave amplitude of the noise pattern, e.g., within a reduced-noise zone 110, as described in detail below. Speaker 108 may include any suitable speaker, e.g., as is known in the art. For example, speaker 108 may include speaker Part No. AI 4.0, available from Cerwin-Vega Inc., Chatsworth, Calif.

According to some exemplary embodiments of the invention, controller 106 may be able to evaluate a noise error corresponding to an anticipated destructive interference between the noise pattern and the noise destructive pattern at a predetermined location 112 within zone 110, as described below. The noise error may be evaluated, for example, by controller 106, e.g., based on noise signal 103, as described below. Additionally or alternatively, the noise error may be sensed by an error-sampling microphone positioned at the predetermined location, as described below. Controller 106 may control speaker 108 to produce the noise destructive pattern, e.g., based on noise signal 103 and/or on the evaluated noise error, as described below.

According to some exemplary embodiments of the invention, it may be desired to control the timing at which the noise destructive pattern is produced, e.g., in order to efficiently control, e.g., reduce, the noise within zone 110. For example, it may be desired to controllably time the noise destructive pattern corresponding to a sample of the noise pattern such that the destructive noise pattern reaches a location within zone 110, e.g., location 112, at substantially the same time the sampled noise pattern reaches the same location.

According to embodiments of the invention, there may be a time delay between the time at which a currently sampled noise pattern reaches location 112 and the time at which the noise destructive pattern corresponding to the current sample of the noise pattern reaches location 112. This time delay may result, for example, from the time required for microphone 102 to sense the noise pattern, the time required for controller to process noise signal 103, and/or the time required for speaker 108 to produce the noise destructive pattern.

Thus, according to some exemplary embodiments of the invention, controller 106 may estimate a sample of the noise pattern succeeding the current sample (“the succeeding sample”) based on the current sample and/or one or more previous samples of the noise pattern. Controller 118 may provide an input to speaker 113, such that speaker 113 produces the noise destructive pattern based on the estimated succeeding sample, e.g., such that the noise destructive pattern may reach location 112 substantially at the same time the noise pattern reaches location 112.

An acoustic pattern, e.g., the noise pattern, may be characterized by a generally non-linear function. Thus, according to exemplary embodiments of the invention, controller 106 may use non-linear estimation to estimate the succeeding sample. Such non-linear estimation may provide, according to exemplary embodiments of the invention, a better estimation of the succeeding sample compared to a corresponding linear estimation. However, according to other embodiments of the invention, controller 106 may use any other suitable estimation, e.g., a linear estimation, to estimate the succeeding sample.

According to exemplary embodiments of the invention, controller 106 may include an estimator 121 to produce a predicted noise signal 114 by applying an estimation function to one or more samples of noise signal 103. Speaker 113 may produce the noise destructive pattern based on predicted noise signal 114, as described below.

Figure 2:
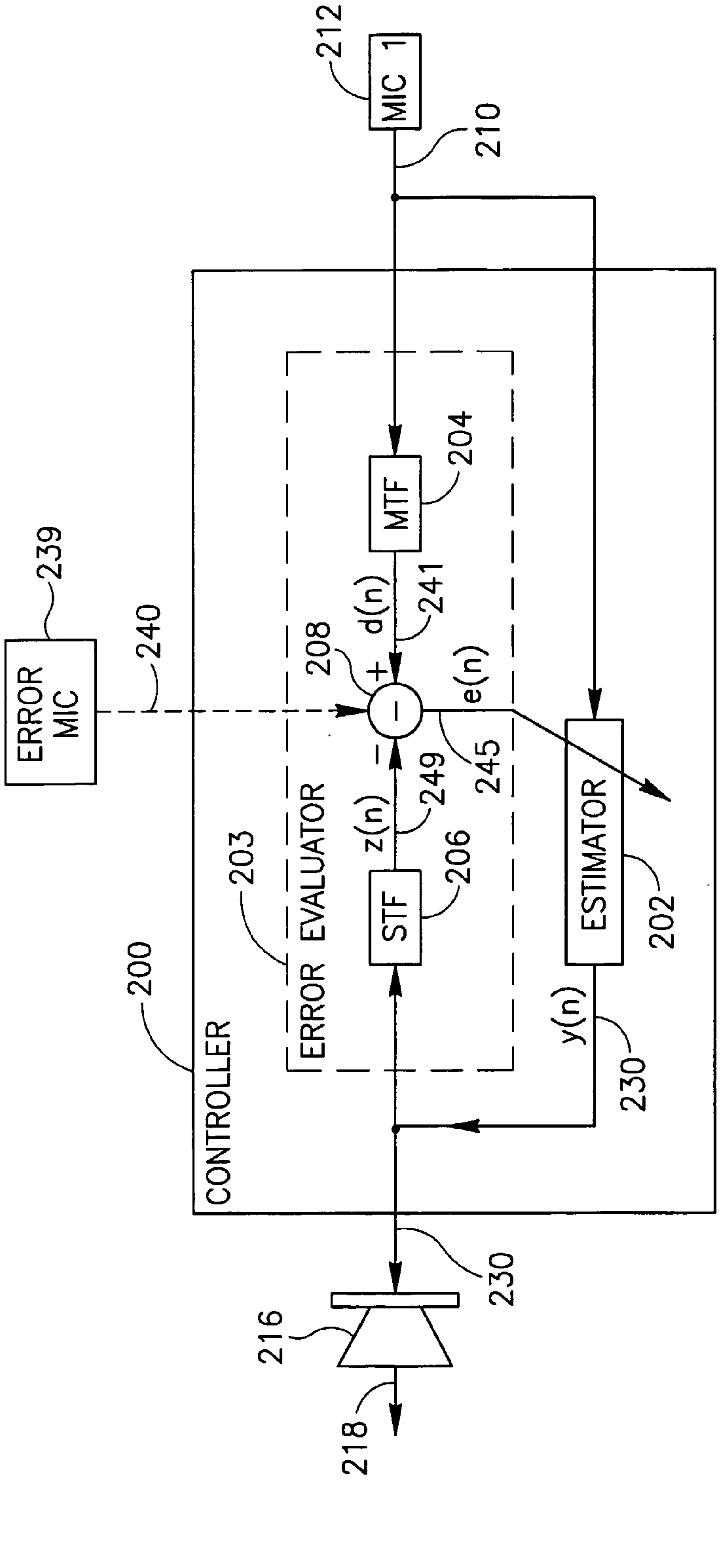
FIG. 2 is a schematic illustration of a controller according to some exemplary embodiments of the invention that may be used, for example, in conjunction with the system of FIG. 1.

Reference is made to FIG. 2, which schematically illustrates a controller 200 according to some exemplary embodiments of the invention. Although the invention is not limited in this respect, controller 200 may be implemented by ANC system 100 (FIG. 1).

According to exemplary embodiments of the invention, controller 200 may include an estimator 202 to receive from an acoustic sensor, e.g., a microphone 212, a noise signal 210, e.g., including a plurality of samples of a sensed noise pattern. Estimator 202 may generate a predicted noise signal 230 having a value, y(n), corresponding to an n-th sample, denoted MIC(n), received from microphone 212, by applying an estimation function F to the sample MIC(n) and to one or more other samples previously received from microphone 212, as described below. Controller 202 may control an acoustic transducer, e.g., a speaker 216, to generate a noise destructive pattern 218, e.g., based on output 230.

According to some exemplary embodiments of the invention, estimator 202 may implement a non-linear estimation algorithm, as described below.

According to some exemplary embodiments of the invention, estimator 202 may implement a Radial Basis Function (RBF) algorithm, as described below.

Estimator 202 may implement the RBF algorithm to estimate the value of a succeeding sample of the noise signal based on the values of one or more samples of the noise signal received from microphone 212. For example, the RBF algorithm may correspond to a combination of a set of K radial n-dimension functions, wherein each function may differ in one or more parameters, e.g., a center of the function parameter, denoted $c_k$, an effective radius parameter, denoted $v_k$, and/or and intensity of the function, denoted $w_k$, as are known in the art. For example, estimator 202 may implement a RBF algorithm analogous to the one described by S. Haykin, "*Adaptive Filter Theory", 3rd edition,* Prentice Hall, pp. 863-565.

According to some exemplary embodiments of the invention, estimator 202 may generate predicted noise 230 according to the following equation:

$$y[n] = \sum_{k=1}^{K} w_k \exp\left(-\frac{1}{2v_k}\sum_{i=0}^{L-1}(MIC[n-i]-c_k[i])^2\right) \tag{1}$$

wherein L denotes a determined number of samples of the noise signal to be implemented for the estimation of y(n).

According to some exemplary embodiments of the invention, estimator 202 may iteratively adapt one or more parameters, e.g., one or more of the parameters $c_k$, $v_k$, and $w_k$, of the estimation function F, e.g., based on a predetermined criterion, as described below.

According to some exemplary embodiments of the invention, estimator 202 may iteratively adapt one or more of the parameters $c_k$, $v_k$, and $w_k$ based on the evaluated noise error at a predetermined location, e.g., location 112 (FIG. 1), as described below.

According to some exemplary embodiments of the invention, controller 200 may also include an error evaluation module 203 to evaluate the noise error, e.g., based on noise signal 210 and predicted noise signal 230, as described below.

According to some exemplary embodiments of the invention, module 203 may include, for example, a Modulation Transfer Function (MTF) module 204 to apply to noise signal 210 a predetermined MTF, thereby to generate an output 241 having a value corresponding to an estimation, denoted d(n), of the n-th sample of the noise pattern at the predetermined location. The MTF may be determined, for example, based on characteristics of microphone 212 and/or based on geometrical and/or physical characteristics of a path and/or a medium, e.g., air, between microphone 212 and the predetermined location, e.g., as known in the art. MTF module 204 may include any suitable hardware and/or software, e.g., as are known in the art, to apply a predetermined MTF to noise signal 210.

According to exemplary embodiments of the invention, module 203 may also include a Speaker Transfer Function (STF) module 206 to apply a STF to predicted noise signal 230, thereby to generate an output 249 having a value corresponding to an estimation of noise destructive pattern 218 produced in response to predicted noise signal 230. The STF may be determined, for example, based on characteristics of speaker 216, e.g., as known in the art. STF module 206 may include any suitable hardware and/or software, e.g., as are known in the art, to apply a predetermined STF to predicted noise signal 230. For example, the value, denoted z(n), of output 249 may be calculated using the following equation:

$$z(n) = \sum_{s=0}^{S-1} STF(s)y(n-s) \tag{2}$$

wherein S denotes a predetermined STF frequency parameter vector, as is known in the art.

Substituting Equation 1 in Equation 2 may yield the following equation:

$$z(n) = \sum_{s=0}^{S-1} STF(s)\sum_{k=1}^{K} w_k \exp\left(-\frac{1}{2v_k}\sum_{i=0}^{L-1}(x(n-s-i)-c_k(i))^2\right) \tag{3}$$

According to exemplary embodiments of the invention, module 203 may also include a subtractor 208, which may be implemented by any suitable hardware and/or software as are known in the art. Subtractor 208 may subtract the value of the estimated noise destructive pattern, e.g., of output STF 249, from the estimated value of the noise pattern, e.g., of output 241, to produce an output 245 including the evaluated noise error, denoted e(n), corresponding to sample MIC(n).

According to exemplary embodiments of the invention, estimator 202 may implement an adaptive algorithm to iteratively adapt the values of one or more of the parameters $v_k$, $c_k$, and $w_k$, e.g., based on the value of the noise error, as described below.

According to exemplary embodiments of the invention, the value of the noise error e(n), corresponding to the n-th sample of noise signal 210 may be estimated using the following equation:

$$e(n)=d(n)-z(n) \tag{4}$$

Substituting Equation 3 in Equation 4 may yield the following equation:

$$e(n) = d(n) - \sum_{s=0}^{S-1} STF(s)\sum_{k=1}^{K} w_k \exp\left(-\frac{1}{2v_k}\sum_{i=0}^{L-1}(x(n-s-i)-c_k(i))^2\right) \tag{5}$$

According to some exemplary embodiments of the invention, estimator 202 may iteratively adapt one or more of the parameters $v_k$, $c_k$, and $w_k$, to reduce, e.g., minimize, the arithmetic mean, denoted $E[(e(n))^2]$, of the square of the noise error. For example, estimator 202 may be able to iteratively adapt one or more of the parameters of the estimation function such that the partial derivative of $E[(e(n))^2]$ with respect to one or more of the parameters, respectively, is equal to zero, as described below.

According to some exemplary embodiments of the invention, the arithmetic mean of the square of the estimated noise error may be calculated using the following equation:

$$E[(e(n))^2] = E\left[\left(d(n) - \sum_{s=0}^{S-1} STF(s) \sum_{k=1}^{K} w_k f_k[n-s]\right)^2\right] \tag{6}$$

wherein $$f_k[n-s] = \exp\left(-\frac{1}{2\upsilon_k}\sum_{i=0}^{L-1}(x(n-s-i)-c_k(i))^2\right) \tag{7}$$

The partial derivatives of Equation 6 with respect to the parameters $c_k$, $v_k$, and $w_k$, respectively, may be calculated using the following equations:

$$\frac{\partial E[(e(n))^2]}{\partial w_k} = E\left[-2e(n)\sum_{s=0}^{S-1} STF(s) f_k[n-s]\right] \tag{8}$$

$$\frac{\partial E[(e(n))^2]}{\partial c_k} = -E\left[2e(n)w_k \sum_{s=0}^{S-1} STF(s) f_k[n-s]\left(\frac{1}{\upsilon_k}\sum_{i=0}^{L-1}(x(n-i)-c_k(i))\right)\right] \tag{9}$$

$$\frac{\partial E[(e(n))^2]}{\partial \upsilon_k} = E\left[e(n)w_k \sum_{s=0}^{S-1} STF(s) f_k[n-s]\frac{1}{(\upsilon_k)^2}\sum_{i=0}^{L-1}(x(n-i)-c_k(i))^2\right] \tag{10}$$

A minimum value of $E[(e(n))^2]$ may be determined by from the following equations:

$$\frac{\partial E[(e(n))^2]}{\partial w_k} = 0 \tag{11}$$

$$\frac{\partial E[(e(n))^2]}{\partial c_k} = 0 \tag{12}$$

$$\frac{\partial E[(e(n))^2]}{\partial \upsilon_k} = 0 \tag{13}$$

Applying the condition of Equation 11 to Equation 8 may result in the following relation between an adapted value, denoted $w_k(n+1)$, and the current value, $w_k(n)$, of the parameter $w_k$:

$$w_k(n+1) = w_k(n) - \mu_w e(n)\sum_{s=0}^{S-1} STF(s) f_k[n-s] \tag{14}$$

wherein $\mu_k$ is a determined convergence parameter corresponding to $w_k$.

Applying the condition of Equation 12 to Equation 9 may result in the following relation between an adapted value, denoted $c_k(n+1)$, and the current value, $c_k(n)$, of the parameter $c_k$:

$$c_k(n+1) = c_k(n) - \mu_c e(n) w_k \sum_{s=0}^{S-1} STF(s) f_k[n-s]\left(\frac{1}{\upsilon_k}\sum_{i=0}^{L-1}(x(n-i)-c_k(i))\right) \tag{15}$$

wherein $\mu_c$ is a determined convergence parameter corresponding to $c_k$.

Applying the condition of Equation 13 to Equation 10 may result in the following relation between an adapted value, denoted $v_k(n+1)$, and the current value, $v_k(n)$, of the parameter $v_k$:

$$\upsilon_k(n+1) = \upsilon_k(n) - \mu_\upsilon e(n) w_k \sum_{s=0}^{S-1} STF(s) f_k[n-s]\frac{1}{(\upsilon_k)^2}\sum_{i=0}^{L-1}(x(n-i)-c_k(i))^2 \tag{16}$$

wherein $\mu_v$ is a determined convergence parameter corresponding to $v_k$.

According to some exemplary embodiments of the invention, adaptive estimator 202 may implement one or more of Equations 14-16 to iteratively adapt one or more of the parameters $w_k$, $c_k$, and $v_k$, respectively.

Some exemplary embodiments of the invention relate to an ANC system, e.g., system 100 (FIG. 1), implementing an error evaluation module, e.g., module 203, to evaluate the noise error at a predetermined location, e.g., location 112 (FIG. 1). However, it will be appreciated by those skilled in the art, that according to other embodiments of the invention, any other one or more suitable modules may be implemented to evaluate the noise error. For example, an error-sensing microphone 239 may be located at the predetermined location, and an output 240 of error-sensing microphone 239 corresponding to the sensed noise error at the predetermined location may be provided to estimator 202.

Some exemplary embodiments of the invention relate to an ANC system, e.g., ANC system 100 (FIG. 1), including a controller, e.g., controller 106 (FIG. 1), to control an acoustic transducer, e.g., speaker 108 (FIG. 1), based on a noise signal of a noise pattern received from an acoustic sensor, e.g., microphone 102 (FIG. 1). However, other embodiments of the invention may refer to an ANC system including a controller able to control an acoustic transducer based on one or more noise signals of a noise pattern received from more than one acoustic sensor, e.g., as described below.

Figure 3:
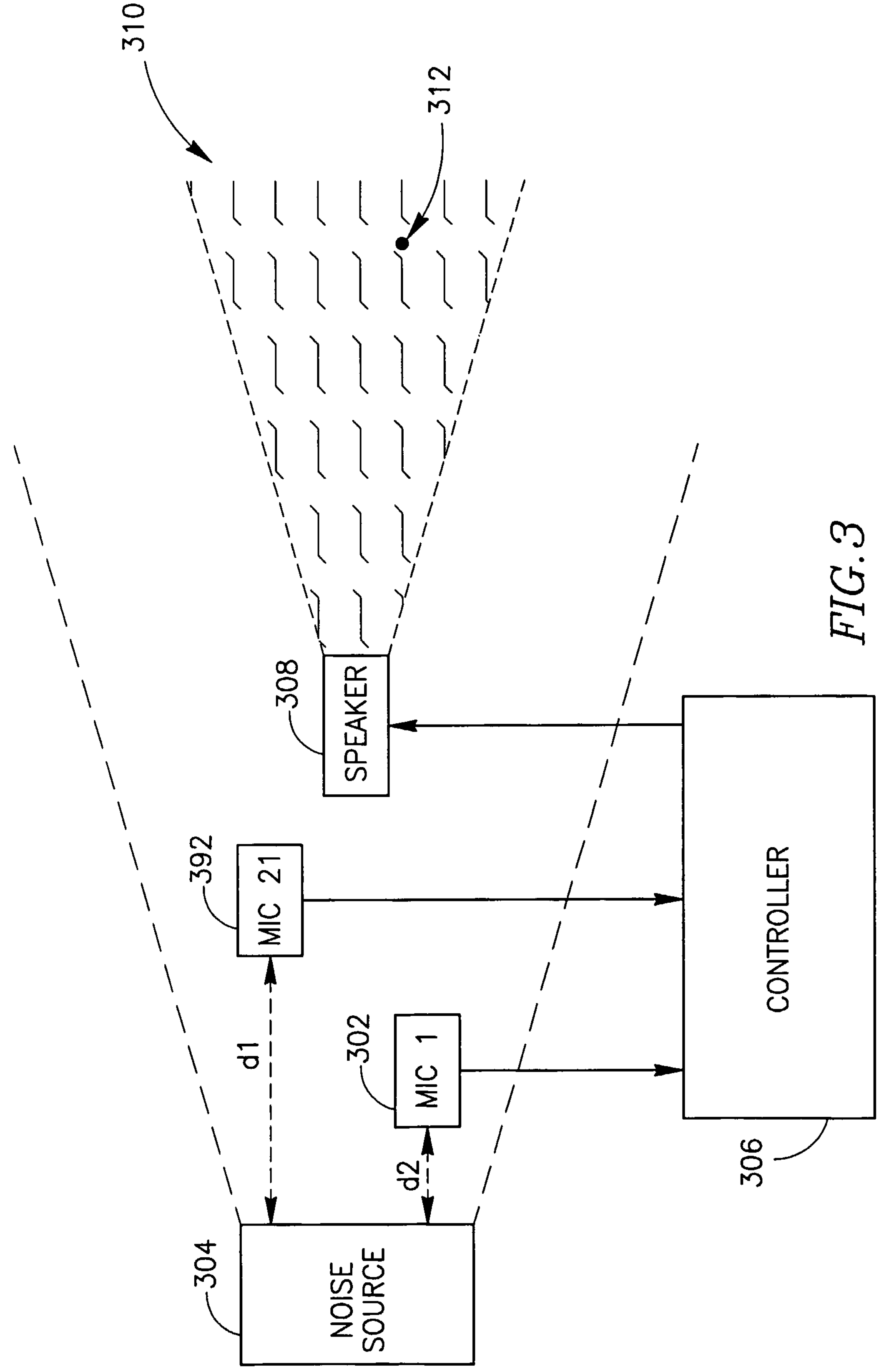
FIG. 3 is a schematic illustration of an active noise control system according to another exemplary embodiment of the invention.

Reference is made to FIG. 3, which schematically illustrates an ANC system 300 according to another exemplary embodiment of the invention.

ANC system 300 may include, for example, a primary acoustic sensor, e.g., a microphone 302, denoted MIC1, to sample the noise energy and/or wave amplitude of a noise pattern produced by a noise source 304. Microphone 302 may include any suitable microphone, e.g., as described above with reference to microphone 102 (FIG. 1).

ANC system 300 may also include an acoustic transducer, e.g., a speaker 308, and a controller 306 able to control speaker 308 to produce a noise destructive pattern to reduce or cancel the noise energy and/or wave amplitude of the noise pattern, e.g., within a reduced-noise zone 310, as described in detail below. Speaker 308 may include any suitable speaker, e.g., as described above with reference to speaker 108 (FIG. 1).

According to some exemplary embodiments of the invention, controller 306 may be able to evaluate a noise error corresponding to a combination of, e.g., a difference between, the noise pattern and the noise destructive pattern, e.g., at a predetermined location 312 within zone 310, as described below. Controller 306 may control speaker 308 to produce the noise destructive pattern, for example, such that the noise error is reduced, e.g., minimized, as described below.

According to exemplary embodiments of the invention, a relatively good coherence between primary microphone 302 and the evaluation of the noise error, e.g., at the relevant frequencies of the noise pattern, may be required in order for ANC 300 to achieve an efficient degree of noise reduction, as described below. For example, the higher correlation between the noise pattern sampled by microphone 302 and the noise error, the higher the level of noise control, e.g., noise reduction, which may be achieved by ANC system 300. The coherence between the noise pattern sampled by microphone 302 and the noise error may depend, for example, on the geometric structure of the path between microphone 302 and location 312. Additionally or alternatively, the coherence between the noise pattern received by microphone 302 and the noise error may depend, for example, on the aerodynamic attributes, e.g., surface roughness, of the path. For example, no "eye contact" between microphone 302 and location 312 and/or a path having relatively rough surfaces may result in a reduced coherence between the signal received by microphone 302 and the evaluated noise error. Furthermore, the operation of ANC 300 to reduce the noise may be disturbed by formation of acoustic signals along the path between the microphone 302 and location 312, e.g., due to turbulent airflow and/or friction between the air and path materials, for example, if a structure of a device implementing one or more elements of ANC 300 does not have an aerodynamically optimized design, e.g., due to price and size constraints. Turbulent airflow may be characterized by stochastic formation of eddies which produce significant rustles, and friction between the air and the relatively rough surfaces may be characterized by conversion of kinetic energy into heat and noise energy.

According to exemplary embodiments of the invention, the noise error may be evaluated using a MTF, e.g., as described below with reference to FIG. 4. The MTF may be predetermined, e.g., based on one or more characteristics of the path between microphone 302 and location 312, and/or one or more expected characteristics of the noise pattern. However, one or more of the characteristics of the path and/or the expected characteristics of the noise pattern may be different than the expected characteristics. As a result, the correlation between the noise error, e.g., evaluated based on the predetermined MTF, and the actual noise at location 312 may not be sufficiently accurate.

According to some exemplary embodiments of the invention, ANC system 300 may also include at least one secondary acoustic sensor, e.g., at least one secondary microphone 392, denoted MIC21, to sample the noise energy and/or wave amplitude of the noise pattern produced by noise source 304. Secondary microphone 392 may be separated from noise source 304 by a distance, d1, bigger than the distance, d2, between primary microphone 302 and noise source 304. For example, microphone 392 may be located along the path between microphone 302 and location 312. The distance d1-d2 between microphone 392 and microphone 302 may be large enough to allow microphone 392 to sample a residual noise pattern, e.g., a noise pattern formed by the path, which may not be received by microphone 302. Microphone 392 may include any suitable microphone, e.g., as described above with reference to microphone 102 (FIG. 1).

According to some exemplary embodiments of the invention, controller 306 may control speaker 308 to produce the noise destructive pattern based on the noise pattern sensed by microphone 302 and/or the residual noise pattern sensed by microphone 392, as described below.

Figure 4:
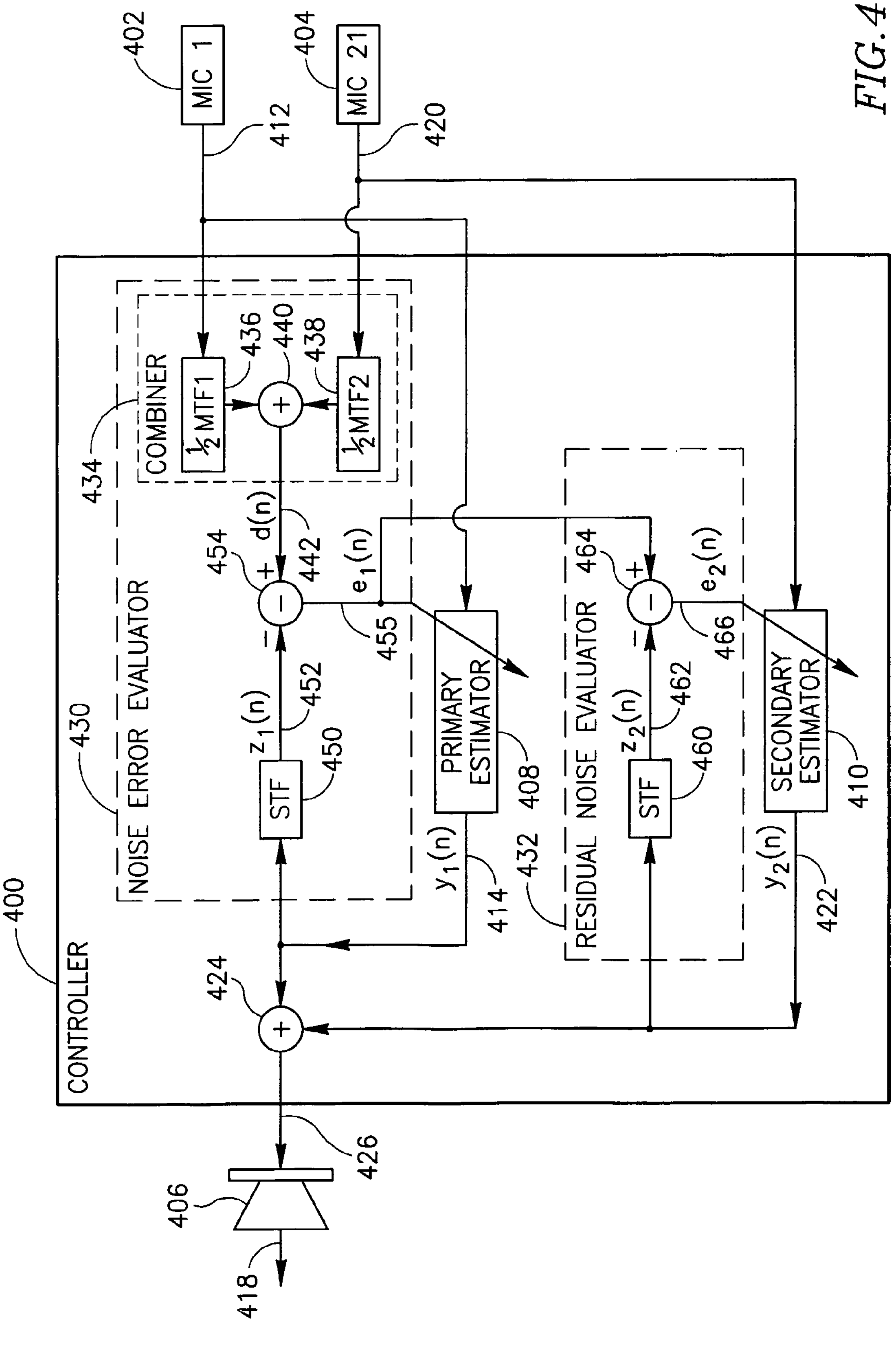
FIG. 4 is a schematic illustration of a controller according to other exemplary embodiments of the invention that may be used, for example, in conjunction with the system of FIG. 3.

Reference is made to FIG. 4, which schematically illustrates a controller 400 according to another exemplary embodiment of the invention. Although the invention is not limited in this respect, controller 400 may be implemented by ANC system 300 (FIG. 3).

According to exemplary embodiments of the invention, controller 400 may include a reference estimator 408 to receive from a primary microphone 402 a primary noise signal 412, e.g., including a plurality of samples. Estimator 408 may generate a predicted primary signal 414 having a value, $y_1(n)$, corresponding to an n-th sample, denoted MIC1($n$), received from microphone 402, by applying a primary estimation function $F_1$ to the sample MIC1($n$) and to one or more other samples previously received from microphone 402, as described below.

According to exemplary embodiments of the invention, controller 400 may also include at least one secondary estimator 410 to receive from at least one secondary microphone 404 at least one secondary noise signal, respectively, e.g., including a plurality of samples. Estimator 410 may generate a predicted secondary signal 422 having a value, $y_2(n)$, corresponding to an n-th sample, denoted MIC21($n$), received from microphone 404, by applying a secondary estimation function $F_2$ to the sample MIC21($n$) and to one or more other samples previously received from microphone 404, as described below.

Controller 400 may control an acoustic transducer, e.g., a speaker 406, to generate a noise destructive pattern 418, e.g., based on a combination of signal 414 and signal 422. For example, controller 400 may also include an adder 424, e.g., as is known in the art, to provide speaker 406 with an input 426 corresponding to the sum of signals 422 and 414.

According to some exemplary embodiments of the invention, estimator 408 may generate signal 414 according to the following equation:

$$y_1(n) = \sum_{s=0}^{L_1} W_1(s) MIC1(n-s) \quad (17)$$

wherein $W_1$ denotes a predetermined prediction filter (PF) vector of length $L_1$ corresponding to estimation function $F_1$.

According to some exemplary embodiments of the invention, estimator 410 may generate signal 422 according to the following equation:

$$y_2(n) = \sum_{s=0}^{L_2} W_2(s) MIC21(n-s) \quad (18)$$

wherein $W_2$ denotes a predetermined PF vector of length $L_2$ corresponding to estimation function $F_2$.

According to some exemplary embodiments of the invention, estimator 408 may iteratively adapt the vector $W_1$, and/or estimator 410 may iteratively adapt the vector $W_2$, e.g., based on a predetermined criterion, as described below.

According to some exemplary embodiments of the invention, estimator 408 may iteratively adapt vector $W_1$, based on the noise error corresponding to the combination of, e.g., the difference between, the noise pattern at the predetermined location, e.g., location 312 (FIG. 3), and an estimation of the contribution of signal $y_1(n)$ to noise destructive pattern 418, as described below.

According to some exemplary embodiments of the invention, controller 400 may also include a first evaluation module 430 to evaluate the noise error, e.g., based on signal 412 and signal 414, as described below.

According to some exemplary embodiments of the invention, module 430 may include, for example, a combiner 434 to combine signals 412 and 420. For example, combiner 434 may include a first MTF module 436 to apply a first predetermined MTF, denoted $MTF_1$, to signal 412 and to divide the result by two. Combiner 434 may also include a second MTF module 438 to apply a second predetermined MTF, denoted $MTF_2$, to signal 420 and to divide the result by two. For example, $MTF_1$, may be determined, e.g., as known in the art, based on characteristics of microphone 402 and/or based on geometrical and/or physical characteristics of a path between microphone 412 and the certain location. $MTF_2$, may be determined, for example, based on characteristics of microphone 404 and/or based on geometrical and/or physical characteristics of a path between microphone 404 and the predetermined location. Combiner 434 may also include an adder 440 to generate an output 442, denoted d(n), corresponding to an average between an estimation the n-th sample of the noise pattern at the certain location using $MTF_1$, and an estimation the n-th sample of the noise pattern at the certain location using $MTF_2$.

For example, d(n) may be calculated using the following equation:

$$d(n)=\frac{1}{2}\left(\sum_{s=0'}^{M_1}(MTF_1(s)Mic1(n-s))+\sum_{s=0'}^{M_2}(MTF_2(s)Mic21(n-s))\right) \quad (19)$$

wherein $M_1$ denotes a predetermined number of samples of $MTF_1$, and $M_2$ denotes a predetermined number of samples of $MTF_2$.

According to exemplary embodiments of the invention, module 430 may also include a STF module 450 to apply a STF to signal 414 to generate an output 452 representing an estimation of a primary part of the noise destructive pattern corresponding to predicted primary signal 414. The STF may be determined, for example, based on characteristics of speaker 406, e.g., as known in the art. STF module 450 may include any suitable hardware and/or software, e.g., as known in the art, to apply a predetermined STF to signal 414. For example, the value, denoted $z_1(n)$, of output 452 may be calculated using the following equation:

$$z_1(n)=\sum_{p=0}^{S-1}STF(p)y_1(n-p) \quad (20)$$

Substituting Equation 17 in Equation 20 may yield the following equation:

$$z_1(n)=\sum_{p=0}^{S-1}STF(p)\sum_{s=0}^{L_1}W_1(s)MIC1(n-s-p) \quad (21)$$

According to exemplary embodiments of the invention, module 430 may also include a subtractor 454, e.g., implemented by any suitable hardware and/or software as known in the art. Subtractor 454 may subtract the value of output 452, from the value of output 442, to produce an output 455 including the evaluated noise error, denoted $e_1(n)$, corresponding to samples MIC1($n$) and MIC21($n$).

According to exemplary embodiments of the invention, estimator 408 may implement an adaptive algorithm to iteratively adapt the value of vector $W_1$, e.g., based on the value of $e_1(n)$, as described below.

According to exemplary embodiments of the invention, the noise error, e (n), corresponding to the n-th samples received from microphones 402 and 404 may be evaluated using the following equation:

$$e_1(n)=d(n)-z_1(n) \quad (22)$$

Substituting Equation 21 in Equation 22 may yield the following equation:

$$e_1(n)=d(n)-\sum_{p=0}^{S-1}STF(p)\sum_{s=0}^{L_1}W_1(s)MIC1(n-s-p) \quad (23)$$

According to some exemplary embodiments of the invention, estimator 408 may iteratively adapt the value of vector $W_1$, to reduce, e.g., minimize, the evaluated noise error $e_1(n)$. For example, estimator 408 may be able to iteratively adapt the value of vector $W_1$ using the following equation:

$$W_1(n+1)=W_1(n)-\mu_1\sum_{p=0}^{S-1}STF(s)MIC1(n-s)e_1(n) \quad (24)$$

wherein $W_1(n+1)$ denotes an adapted value of $W_1$, $W_1(n)$ denotes the current value of $W_1$, and $\mu_1$ denotes a predetermined convergence parameter corresponding to $W_1$. For example, $\mu_1$ may be determined according the following condition:

$$\mu_1<\frac{1}{2L_1} \quad (25)$$

According to some exemplary embodiments of the invention, estimator 410 may iteratively adapt the value of vector $W_2$ of the estimation function $F_2$, based on an evaluated residual noise error corresponding to the combination of, e.g., the difference between, the evaluated noise error $e_1(n)$, and an estimation of the contribution of $y_2(n)$ to noise destructive pattern 418, as described below.

According to some exemplary embodiments of the invention, controller 400 may also include at least one secondary evaluation module 432 to evaluate the residual noise error, e.g., based on signal 422 and the evaluated noise error $e_1(n)$, as described below.

According to exemplary embodiments of the invention, module 432 may include a STF module 460 to apply a STF to signal 422 to generate an output 462 representing an estimation of a secondary part of the noise destructive pattern corresponding to signal 422. STF module 460 may include any suitable hardware and/or software, e.g., as known in the art, to apply a predetermined STF to signal 422. The STF may be predetermined, for example, based on characteristics of speaker 406, e.g., as known in the art. For example, the value, denoted $z_2(n)$, of output 462 may be calculated using the following equation:

$$z_2(n) = \sum_{p=0}^{S-1} STF(p) y_2(n-p) \tag{26}$$

Substituting Equation 18 in Equation 26 may yield the following equation:

$$z_2(n) = \sum_{p=0}^{S-1} STF(p) \sum_{s=0}^{L_2} W_2(s) MIC21(n-s-p) \tag{27}$$

According to exemplary embodiments of the invention, module 432 may also include a subtractor 464, e.g., implemented by any suitable hardware and/or software as known in the art. Subtractor 464 may subtract the value of output 462, from the value of output 452, to produce an output 466 including the evaluated residual noise error, denoted $e_2(n)$, corresponding to samples MIC1(*n*) and MIC21(*n*).

According to exemplary embodiments of the invention, estimator 410 may implement an adaptive algorithm to iteratively adapt the value of vector $W_2$, e.g., based on the value of $e_2(n)$, as described below.

According to exemplary embodiments of the invention, the residual noise error, $e_2(n)$, corresponding to the n-th samples received from microphones 402 and 404 may be evaluated using the following equation:

$$e_2(n) = e_1(n) - z_2(n) \tag{28}$$

Substituting Equations 23 and 27 in Equation 28 may yield the following equation:

$$e_2(n) = d(n) - \sum_{p=0}^{S-1} STF(p) \sum_{s=0}^{L_1} W_1(s) MIC1(n-s-p) - \sum_{p=0}^{S-1} STF(p) \sum_{s=0}^{L_2} W_2(s) MIC21(n-s-p) \tag{29}$$

According to some exemplary embodiments of the invention, estimator 410 may iteratively adapt the value of vector $W_2$, to reduce, e.g., minimize, the evaluated residual noise error $e_2(n)$. For example, estimator 410 may be able to iteratively adapt one or more elements of vector $W_1$ using the following equation:

$$W_2(n+1) = W_2(n) - \mu_2 \sum_{p=0}^{S-1} STF(p) MIC21(n-s-p) e_2(n) \tag{30}$$

wherein $W_2(n+1)$ denotes an adapted value of $W_2$, $W_2(n)$ denotes the current value of $W_2$, and $\mu_2$ denotes a predetermined convergence parameter corresponding to $W_2$. For example, $\mu_2$ may be determined according the following condition:

$$\mu_2 < \frac{1}{2L_2} \tag{31}$$

Some of the embodiments described above may refer to ANC systems implementing a controller, e.g., controller 400, able to control an acoustic transducer, e.g., speaker 406, to generate a noise destructive pattern based on a combination of an a primary noise signal of a primary acoustic sensor, e.g., microphone 402, and a secondary noise signal of a secondary acoustic sensor, e.g., microphone 404. However, it will be appreciated by those skilled in the art that according to other embodiments of the invention, these systems may be modified to implement one or more additional secondary acoustic sensors. For example, controller 400 may be modified to include an additional plurality of secondary estimators to receive one or more primary noise signals of the one or more additional secondary microphones, respectively. For example, an i-th estimator of the additional secondary estimators may generate, for example, an output, denoted $y_i(n)$, corresponding to the following equation:

$$y_i(n) = \sum_{s=0}^{L_1} W_i(s) MICi(n-s) \tag{32}$$

wherein Wi denotes a predetermined prediction filter (PF) vector of length $L_i$ corresponding to the i-th estimator, and MICi denotes the output of the i-th additional secondary microphone.

Controller 400 may also be modified to include one or more additional residual noise error evaluators to evaluate a residual noise error, e.g., in analogy to evaluator 410. For example, an i-th residual error evaluator may evaluate the i-th residual noise error, $e_i(n)$, using the following equation:

$$e_i(n) = e_{i-1}(n) - \sum_{p=0}^{S-1} STF(p) \sum_{s=0}^{L_1} W_i(s) MICi(n-s-p) \tag{33}$$

According to some exemplary embodiments, an i-th estimator of the additional estimators may iteratively adapt the value of the vector $W_i$, e.g., using the following equation:

$$W_i(n+1) = W_i(n) - \mu_i \sum_{p=0}^{S-1} STF(s) MICi(n-s)_i \tag{34}$$

wherein $W_i(n+1)$ denotes an adapted value of $W_i$, $W_i(n)$ denotes the current value of $W_i$, and $\mu_i$ denotes a predetermined convergence parameter corresponding to $W_i$. For example, $\mu_i$ may be determined according the following condition:

$$\mu_i < \frac{1}{2L_i} \tag{35}$$

Some of the embodiments described above may refer to ANC systems implementing a controller, e.g., controller 400, including one or more estimators, e.g., estimators 408 and/or 410, to apply an adaptive linear estimation algorithm to one or more respective noise signals, e.g., outputs 412 and/or 420. However, it will be appreciated by those skilled in the art that according to other embodiments of the invention, these systems may be modified to implement one or more estimators to apply an adaptive non-linear estimation algorithm to one or more respective noise signals. For example, controller 400 may be modified to implement one or more RBF estimation algorithms, e.g., in analogy to controller 200 (FIG. 2).

Embodiments of the present invention may be implemented by software, by hardware, or by any combination of software and/or hardware as may be suitable for specific applications or in accordance with specific design requirements. Embodiments of the present invention may include modules, units and sub-units, which may be separate of each other or combined together, in whole or in part, and may be implemented using specific, multi-purpose or general processors, or devices as are known in the art. Some embodiments of the present invention may include buffers, registers, storage units and/or memory units, for temporary or long-term storage of data and/or in order to facilitate the operation of a specific embodiment.

While certain features of the invention have been illustrated and described herein, many modifications, substitutions, changes, and equivalents may occur to those of ordinary skill in the art. It is, therefore, to be understood that the appended claims are intended to cover all such modifications and changes as fall within the true spirit of the invention.

What is claimed is:

1. An active noise control system for controlling noise produced by a noise source, said system comprising:

an acoustic sensor to sense a noise pattern and to produce a noise signal corresponding to the sensed noise pattern;

an estimator to produce a predicted noise signal by applying an estimation function to said noise signal, wherein the predicted noise signal includes an estimation of a predicted sample of the noise signal, which is successive to a current sample of the noise signal, and wherein the estimator is to estimate the predicted sample by applying the estimation function to the current sample and to one or more samples preceding the current sample of the noise signal; and an acoustic transducer to produce a noise destructive pattern based on said predicted noise signal.

2. The system of claim 1, wherein said estimator is to adapt one or more parameters of said estimation function based on a noise error at a predetermined location.

3. The system of claim 2, wherein said noise error comprises an anticipated destructive interference between said noise pattern and said noise destructive pattern at said predetermined location.

4. The system of claim 2 comprising an error-sensing microphone to sense said noise error at said predetermined location.

5. The system of claim 2 comprising controller to evaluate said noise error based on said noise signal and said predicted noise signal.

6. The system of claim 5, wherein said controller is to:

produce an estimation of said noise destructive pattern by applying a speaker transfer function to said predicted noise signal;

produce an estimation of said noise pattern at said predetermined location by applying a modulation transfer function to said noise signal; and subtract the estimation of said noise destructive pattern from the estimation of said noise pattern.

7. The system of claim 2, wherein said one or more parameters comprise at least one parameter selected from the group consisting of a center parameter, an effective radius parameter, and an intensity parameter.

8. The system of claim 1, wherein the estimator is to estimate a noise error corresponding to an anticipated destructive interference between the noise pattern and the noise destructive pattern at a predefined location, said predefined location is distinct from a location of said acoustic sensor.

9. The system of claim 1, wherein said acoustic sensor comprises a microphone, and wherein the noise destructive pattern produced by the acoustic transducer has an exponential relationship to the noise pattern sensed by the acoustic sensor.

10. The system of claim 1, wherein said acoustic transducer comprises a speaker, and wherein said acoustic sensor comprises an array of two or more microphones located in two or more locations.

11. An apparatus of active noise control to control a noise, said apparatus comprising:

an estimator to generate a predicted noise signal to be provided to an acoustic transducer of an active noise control system, the predicted noise signal representing a predicted noise based on an input noise signal representing samples of a noise pattern of said noise, said estimator is to estimate said predicted noise by applying an estimation function to said noise signal, wherein the predicted noise includes an estimation of a predicted sample of the noise signal, which is successive to a current sample of the noise signal, and wherein the estimator is to estimate the predicted sample by applying the estimation function to the current sample and to one or more samples preceding the current sample of the noise signal.

12. The apparatus of claim 11, wherein said estimator is to adapt one or more parameters of said estimation function based on a noise error at a predetermined location.

13. The apparatus of claim 12, wherein said noise error comprises an anticipated destructive interference between said noise pattern and a noise destructive pattern, which is based on said predicted noise signal, at said predetermined location.

14. The apparatus of claim 12, wherein said estimator is to receive said noise error from an error-sensing microphone.

15. The system of claim 11, wherein the estimator is to estimate a noise error corresponding to an anticipated destructive interference between the noise pattern and the noise destructive pattern at a predefined location, said predefined location is distinct from a location of sensing said noise pattern.

16. A method of active noise control to control a noise, said method comprising:

generating a predicted noise signal to be provided to an acoustic transducer of an active noise control system, the predicted noise signal representing a predicted noise based on an input noise signal representing samples of a noise pattern of said noise, said generating comprises estimating said predicted noise by applying an estimation function to said noise signal, wherein the predicted noise includes an estimation of a predicted sample of the noise signal, which is successive to a current sample of the noise signal, and wherein the estimating comprises estimating the predicted sample by applying the estimation function to the current sample and to one or more samples preceding the current sample of the noise signal.

17. The method of claim 16 comprising adapting one or more parameters of said estimation function based on a noise error at a predetermined location.

18. The method of claim 17, wherein said noise error comprises an anticipated destructive interference between said noise pattern and a noise destructive pattern, which is based on said predicted noise signal, at said predetermined location.

19. The method of claim 17 comprising receiving said noise error from an error-sensing microphone.

20. The method of claim 16 comprising estimating a noise error corresponding to an anticipated destructive interference between the noise pattern and the noise destructive pattern at a predefined location, said predefined location is distinct from a location of sensing said noise pattern.

* * * * *